United States Patent
Tsutamori

(10) Patent No.: US 6,277,654 B1
(45) Date of Patent: Aug. 21, 2001

(54) METHOD AND APPARATUS FOR DETECTING AN ORGANISM-ORIGINATED SUBSTANCE

(75) Inventor: Yasuhiro Tsutamori, Kaisei-machi (JP)

(73) Assignee: Fuji Photo Film Co., Ltd., Kanagawa-Ken (JP)

( * ) Notice: Subject to any disclaimer, the term of this patent is extended or adjusted under 35 U.S.C. 154(b) by 0 days.

(21) Appl. No.: 09/539,410

(22) Filed: Mar. 30, 2000

(30) Foreign Application Priority Data

Mar. 30, 1999 (JP) .................................................. 11-089357

(51) Int. Cl.⁷ ........................ G01N 33/543; G01N 21/00; G01N 33/53; C12Q 1/68
(52) U.S. Cl. .............................. 436/518; 422/68.1; 435/6; 435/7.1; 435/7.9; 435/7.92; 435/287.2; 435/808; 435/810; 436/164
(58) Field of Search ............................. 435/6, 7.1, 4, 7.2, 435/7.4, 7.5, 7.6, 7.7, 7.71, 7.72, 7.8, 7.92, 91.1, 91.2, 69.1, 810, 285.1, 287.2; 436/501, 518; 430/5; 422/50, 68.1; 536/24.33, 23.1, 24.31, 24.32, 24.3, 24.1, 25.3

(56) References Cited

U.S. PATENT DOCUMENTS

| | | | |
|---|---|---|---|
| 5,143,854 | * | 9/1992 | Pirrung et al. ....................... 436/518 |
| 5,547,839 | * | 8/1996 | Dower et al. ............................. 435/6 |
| 5,800,992 | * | 9/1998 | Fodor et al. ............................. 435/6 |
| 5,874,219 | * | 2/1999 | Rava et al. ............................... 435/6 |
| 6,040,138 | * | 3/2000 | Lockhart et al. ........................ 435/6 |
| 6,092,065 | * | 7/2000 | Floratos et al. ......................... 707/6 |
| 6,136,610 | * | 10/2000 | Polito et al. ......................... 436/514 |

OTHER PUBLICATIONS

Ekins et al. Multianalyte Microspot Immunoassay–Microanalytical "Compact Disk" of the Future. Clin. Chem. vol. 37, No. 11 (1991) pp. 1955–1966.*

Jones et al. Microminiaturized Immunoassays Using Atomic Force Microscopy and Compositionally Patterned Antigen Arrays. Analytical Chemistry. vol. 70, No. 7 (1998) pp. 1233–1241.*

* cited by examiner

Primary Examiner—Long V. Le
Assistant Examiner—Kartic Padmanabhan
(74) Attorney, Agent, or Firm—Sughrue, Mion, Zinn, Macpeak & Seas, PLLC

(57) ABSTRACT

Various types of templates are stored in a template storage section in accordance with various types of array chips varying in disposition of spot positions. In making an analysis in an analysis section, a template, on which ROIs are disposed at positions corresponding to the spot positions on the array chip used, is read out from the template storage section. This template is set onto images represented by labeled data, and a signal value at a position corresponding to the ROI on the template is detected and evaluated.

4 Claims, 7 Drawing Sheets

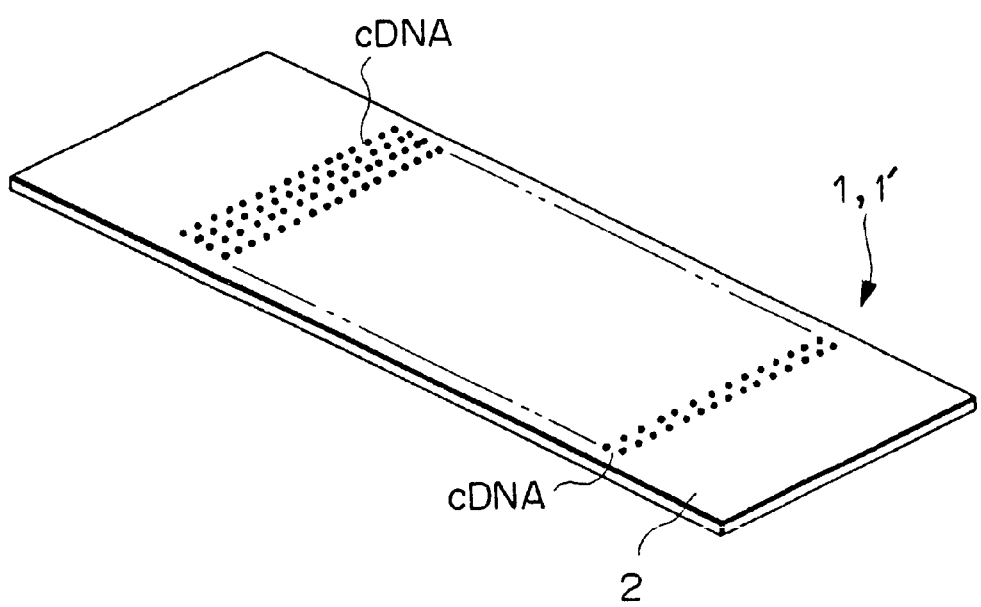
F I G . 1

METHOD AND APPARATUS FOR DETECTING AN ORGANISM-ORIGINATED SUBSTANCE

BACKGROUND OF THE INVENTION

1. Field of the Invention

This invention relates to a method and an apparatus that detect organism-originated substances by using an array chip that is employed in deoxyribonucleic acid (DNA) analysis and immunological analysis.

2. Description of the Related Art

In recent years, techniques in the field of generic engineering have rapidly developed, and the human genome project in which one of the objects is to interpret as many as 100,000 base sequences of the human genome has been developed.

On the other hand, an enzyme immunoassay method, a fluorescent antibody method and the like taking advantage of an antigen-antibody reaction have been utilized in diagnoses and research, and techniques of searching for DNA having influence on various genetic diseases have also advanced. As one of the methods, attention has been paid to an array technique.

In this array technique, an array chip (also called a DNA chip), such as the one shown in FIG. 1, is employed as an array chip 1. In the array chip 1, a large number of known complementary DNAs (an example of a specific binding substance) differing from one another, which have already been interpreted, are disposed with high density in matrix form on a carrier 2 such as a membrane filter, a slide glass and the like. For instance, DNA (an example of an organism-originated substance) originated from the cell of healthy subject A is labeled with a labeling substance consisting of a fluorescent dye or a radioactive isotope, and similarly, DNA originated from the cell of subject B having a genetic disease is labeled with the labeling substance. The labeled DNAs of the subjects A, B are dropped on separate array chips and are hybridized with the complementary cDNAs on the separate array chips. Each hybridized cDNA on each array chip is scanned by laser light that excites each labeling substance, and the fluorescent light or radiation emitted from each cDNA is detected by a photo or radiation detector. Next, a labeled signal representing this result of detection, corresponding to the light-emitting position (spot position) on the array chip, is obtained, and based on this labeled signal, it is judged which cDNA has been hybridized by the cDNA of each subject. The ratio or difference of the labeled signals obtained between both subjects is calculated, and between both subjects, the hybridized cDNAs are compared. In this way, the gene manifested or lost due to the above-mentioned disease (hereinafter referred to as change in manifestation) is specified. Note that if two images represented by the labeled signals are printed or output to a monitor, the change in manifestation can be visually recognized and specified. On the other hand, the ratio between the labeled signals that are obtained from both subjects becomes greater (or smaller) at a position where the change in manifestation exists. Therefore, in the order that the ratio of the labeled signals between both subjects is greater (or smaller), the signal value ratios at 50 spot positions, for example, are caused to correspond to the positions at which the labeled signals were obtained, and these corresponding relations are output as a measurement-result table representing measurement results. Based on this measurement-result table and images displayed on a monitor, the positions at which the labeled signals were obtained are calculated, whereby the change in manifestation can be specified.

The signal value corresponding to each spot position is obtained by setting a template, on which circular ROIs (regions of interest) are disposed at positions corresponding to the spot positions, onto images represented by the labeled signals and detecting a signal value at a position corresponding to the position of the ROI on this template.

However, the above-mentioned method of disposing spot positions on the array chip varies depending on manufacturers of array chips and test purposes. For this reason, if other array chips are employed, in the case where a template is used only for array chips made by a specific manufacturer or for a specific test purpose, the detection of signal values cannot be performed because the spot positions on the array chip do not correspond to the ROI positions on the template. In such a case, if a new template, on which ROIs are disposed at positions corresponding to the spot positions on an array chip used, is generated, signal values can be detected. However, an array chip has as few as 500 spot positions or as many as a few tens of thousand spot positions, and the method of disposing spot positions varies from array chip to array chip. Thus, the operation of generating templates is fairly difficult and time consuming.

SUMMARY OF THE INVENTION

The present invention has been made in view of the aforementioned circumstances. Accordingly, the object of the present invention is to provide a method and an apparatus which are capable of detecting signal values at spot positions even when array chips differing in disposition of spot positions are employed.

To achieve the above object and in accordance with one aspect of the present invention, there is provided a method comprising the steps of:

respectively binding organism-originated substances of a subject labeled with a labeling substance to a plurality of known specific binding substances differing from one another, the specific binding substances being disposed at a plurality of predetermined positions on a carrier on an array chip;

obtaining an image represented by labeled signals emitted from the labeling substances of the organism-originated substances bound to the specific binding substances;

setting a template of a type corresponding to the array chip onto the image, the template having ROIs disposed at positions corresponding to the plurality of predetermined positions on the array chip; and detecting values of the labeling signals at positions on the image which correspond to the ROIs;

wherein the template of a type corresponding to the array chip is read out from template storage means in which various types of templates are stored, and based on the template read out, the signal values are detected.

Here, the ROIs are disposed at positions corresponding to the positions of the specific binding substances disposed on an array chip to be used. The expression "the template of a type corresponding to the array chip is read out" means to read out a template on which ROIs are disposed at positions corresponding to the positions of specific binding substances disposed on an array chip to be used.

Also, the expression "based on the template, the signal values are detected" means to set the template onto an image represented by labeled signals and to detect values of the labeling signals at positions on the image which correspond to the ROIs.

The word "carrier" may be any type if a specific binding substance can be stably bound and spotted on it. For instance, the carrier may be a membrane filter, a slide glass plate, etc. These carriers may be preprocessed to stably bind a specific binding substance.

The aforementioned "specific binding substance" may be hormones, a tumor marker, enzyme, an antibody, an antigen, abzyme, other proteins, a nucleic acid, cDNA, DNA, RNA, etc., and means a substance bindable specifically with an organism-originated substance. The word "known" varies depending on a specific binding substance. For example, in the case of a nucleic acid, the word "known" means that the base sequence, the base length, etc., are known, and in the case of protein, the word "known" means that the composition and the like of the amino acid are known. Here, the expression "specific binding substances disposed at a plurality of predetermined positions on the carrier" means that one kind of specific binding substance has been disposed for each position.

The aforementioned "organism-originated substance" is a substance that binds specifically with a known specific binding substance disposed at a predetermined position on the carrier, and means substances extracted, isolated and the like from a living organism. The "organism-originated substance" includes not only substances extracted directly from a living organism, but also these substances may be chemically processed and chemically modified. For instance, the "organism-originated substance" includes hormones, a tumor marker, enzyme, an antibody, an antigen, abzyme, other proteins, a nucleic acid, cDNA, DNA, mRNA, etc.

The aforementioned "labeling substance" means a marker substance that changes part of an organism-originated substance or is added directly to the organism-originated substance, in order to obtain information from the organism-originated substance. The labeling substance is not particularly limited, as long as a labeled signal emitted therefrom can be detected and also a rule that the labeling substance is taken into an organism-originated substance is known in advance. For example, it is preferable to employ a fluorescent dye, such as cyber green II, Cy5, fluorescein isothiocyanate and the like, and a radioactive isotope such as $^{32}P$, $^{33}P$ and the like.

The aforementioned "labeled signal" means fluorescent light when the labeling substance is a fluorescent dye and radiation when the labeling substance is a radioactive isotope. The labeled signal is obtained by detecting fluorescent light or radiation emitted or output from the labeling substance by a photo or radiation detector.

The expression "binding organism-originated substances to the specific binding substances" means a case (hybridization) such that a stable double strand is formed between complementary nucleotides, as is observed in the case of DNA, RNA or the like. It also means a bond with very high specificity that selectively reacts only to a specific substance, like a bond between an antigen and an antibody, a bond between biotin and abzyme, etc.

In a preferred form of the aforementioned method, the method further comprises the step of generating a new template and storing the new template in the template storage means.

In accordance with another aspect of the present invention, there is provided an apparatus comprising:

binding means which respectively binds organism-originated substances of a subject labeled with a labeling substance to a plurality of known specific binding substances differing from one another, the specific binding substances being disposed at a plurality of predetermined positions on a carrier on an array chip;

analysis means which obtains an image represented by labeled signals emitted from the labeling substances of the organism-originated substances bound to the specific binding substances, sets a template of a type corresponding to the array chip onto the image, and detects values of the labeling signals at positions on the image which correspond to the ROIs, the template having ROIs disposed at positions corresponding to the plurality of predetermined positions on the array chip;

template storage means in which various types of templates are stored;

read means which reads out the template of a type corresponding to the array chip from the template storage means;

wherein the analysis means detects the signal values, based on the template read out.

In a preferred form of the aforementioned apparatus, the apparatus further comprises template generation means which generates a new template and stores the new template in the template storage means.

In the present invention, a template of a type that corresponds to an array chip is read out from the template storage means in which various types of templates are stored. Therefore, if templates corresponding to array chips with a possibility of being used are stored in the template storage means, signal values at positions where specific binding substances are disposed can be detected from labeled signals without generating a new template, regardless of the array chip employed.

In addition, even when the disposition of specific binding substances on an array chip does not correspond to any of the templates stored in the template storage means, signal values at positions where specific binding substances are disposed can be detected from this array chip as well, if a new template can be generated. In such a case, the operation of generating a new template consumes time. However, if the new template has been stored in the template storage means, signal values can be detected from an array chip immediately when the same array chip is used.

BRIEF DESCRIPTION OF THE DRAWINGS

The present invention will be described in further detail with reference to the accompanying drawings wherein:

FIG. 1 is a perspective view showing an array chip employed in a preferred embodiment of the present invention;

DESCRIPTION OF THE PREFERRED EMBODIMENTS

A preferred embodiment of the present invention will hereinafter be described in detail with reference to the drawings.

FIG. 1 shows an array chip employed in the preferred embodiment. In the array chip 1, a plurality of known complementary deoxyribonucleic acids (cDNAs) differing from one another are disposed as specific binding substances at predetermined positions on a carrier 2 such as a membrane filter, a slide glass and the like. Note that the plurality of known cDNAs disposed on the carrier 2 correspond to a plurality of different DNAs whose base sequence has already been interpreted, respectively. Also, the positions at which cDNAs are disposed on the carrier 2 (hereinafter referred to as spot positions) vary depending on manufacturers for the array chip 1.

Figure 2:
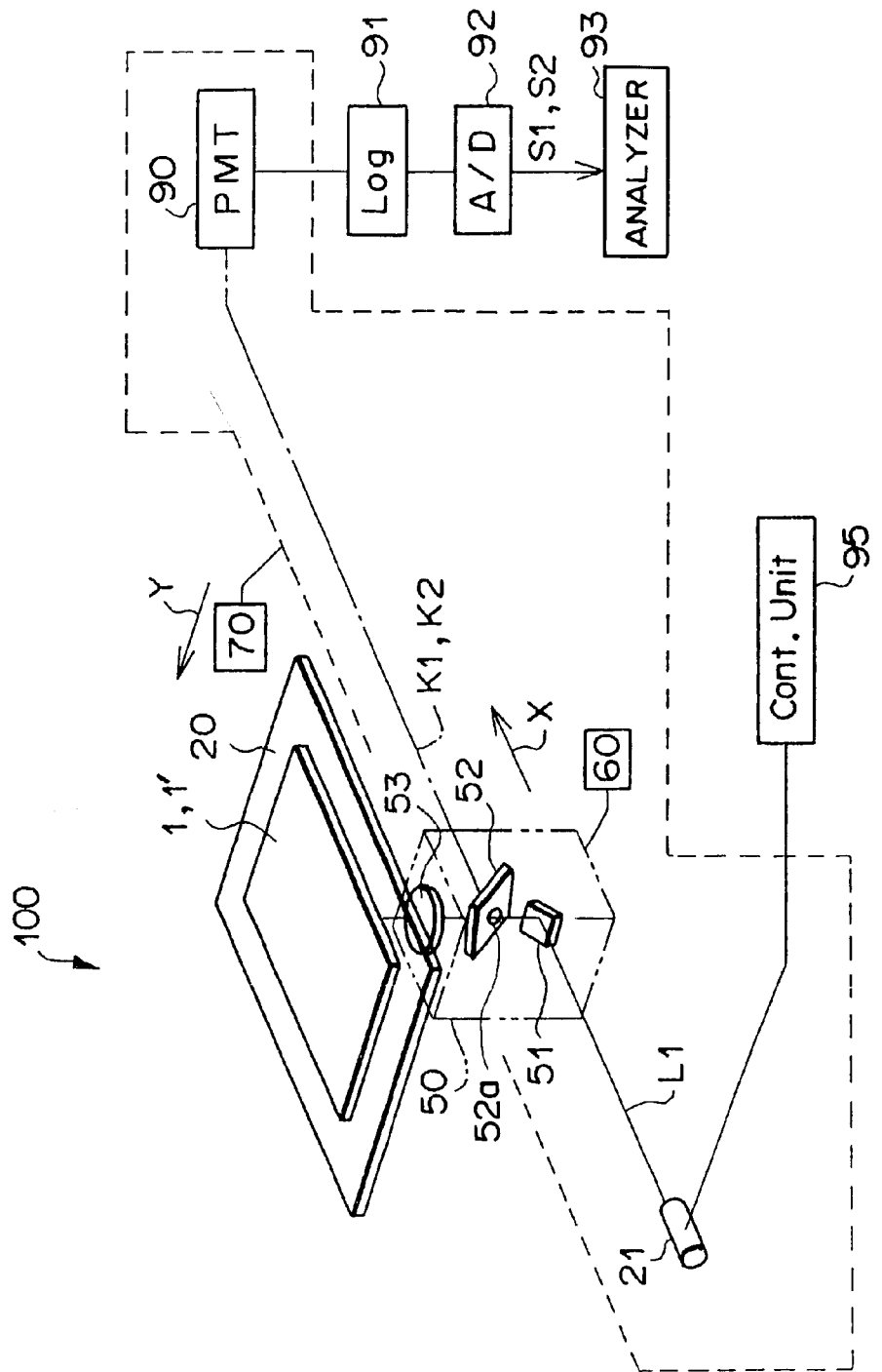
FIG. 2 is a schematic diagram showing a reader employed in the preferred embodiment.

Next, a reader for the array chip 1 shown in FIG. 1 will be described with reference to FIG. 2. The reader 100 shown is an embodiment of a reader for two kinds of array chips 1, 1' to be described later. The reader 100 includes a transparent sample tray 20 which holds the two array chips 1, 1' at predetermined positions, the array chips 1, 1' having the aforementioned plurality of cDNAs hybridized with the cDNAs (organism-originated substances) of 2 different subjects A, B labeled with a fluorescent dye. The reader 100 further includes (1) a laser light source 21 which emits laser light L1 with an emission wavelength suitable to excite the fluorescent dye; (2) a photomultiplier (hereinafter referred to as a PMT) 90 which photoelectrically detects the fluorescent light which the fluorescent dyes on the array chips 1, 1' are excited with and emit; (3) an optical head 50 which directs the laser light L1, emitted from laser light source 21, to the array chips 1, 1' held on the sample tray 20 and also guides the fluorescent light K1, K2, reflected from the array chips 1, 1, to the PTM 90; (4) horizontal scanning means 60 which moves the optical head 50 at a uniform speed in the direction of arrow X; (5) vertical scanning means 70 which moves the laser light source 21, the optical head 50, the filter set 80, and the PMT 90 as one body in the direction of arrow Y perpendicular to the direction of arrow X; (6) an amplifier 91 which logarithmically amplifies signals detected by the PMT 90; (7) an A/D converter 92 which converts the amplified signals and obtains labeled data S1, S2; (8) an analyzer 93 which compares the labeled data S1, S2 obtained at the spot positions corresponding to each other between the array chips 1, 1' and calculates the result of comparison; and (9) a control unit 95 which controls the emission of the laser light L1. Note that the labeled data S1 collectively represents all of the signal values obtained at the spot positions on the array chip 1 where the DNA of the subject A was hybridized. Similarly, the labeled data S2 collectively represents all of the signal values obtained at the spot positions on the array chip 1' where the DNA of the subject B was hybridized.

The subject A is a healthy person, while the subject B is a person with a predetermined genetic disease. As described above, a large number of known cDNAs differing from one another are disposed at predetermined positions on the array chips 1, 1'. Furthermore, cDNAs originated from the cells of the subjects A, B are spotted at the predetermined positions on the array chips 1, 1' by means of a pipette or the like, and among the large number of cDNAs on the array chips 1, 1', the cDNAs corresponding to the cDNAs of the subjects A, B are hybridized with the spotted cDNAs. With a predetermined solution, the cDNA hybridized with the cDNA of either subject is left, while the cDNA not hybridized with the DNA of either subject is washed.

The laser light source 21 can employ, for example, a He—Ne laser that emits laser light L1 of wavelength 633 nm, a SHG laser that emits laser light L1 of wavelength 532 nm, and a SHG laser that emits laser light L1 of wavelength 473 nm. The laser light L1 of wavelength 633 nm is suitable to excite, for example, a fluorescent dye like Cy5, the laser light L1 of wavelength 532 nm is suitable to excite, for example, a fluorescent dye like Cy3, and the laser light L1 of wavelength 473 nm is suitable to excite, for example, a fluorescent dye like fluorescein ($C_{20}H_{12}O_5$).

Next, a description will be given of the operation of the reader 100 of the preferred embodiment.

The array chip 1 with known cDNAs hybridized with the labeled cDNAs of the subject A is placed on the sample tray 20, and the control unit 95 controls the laser light source 21 so that laser light L1 is emitted. With this control, the laser light source 21 emits laser light L1. The laser light L1 emitted from the laser light source 21 travels in the direction of arrow X. The laser light L1 is incident on the plane mirror 51 of the optical head 50 and is reflected upward. The reflected laser light L1 passes through the aperture 52a of a perforated mirror 52 and is incident on a lens 53. With this laser light L1 incident on the lens 53, a very small area on the array chip 1 placed on the sample tray 20 is irradiated. During irradiation, the optical head 50 is being moved at a high and uniform speed in the direction of arrow X by the horizontal scanning means 60, and consequently, the laser light L1 scans the array chip 1 in the direction of arrow X. During this horizontal scanning, with respect to the labeled cDNA in the very small area on the array chip 1 irradiated with the laser light L1, the fluorescent dye is excited by the laser light L1 and emits fluorescent light K1.

The emitted fluorescent light K1 spreads from the lower surface of the array chip 1 and is formed into a downward fluorescent light beam K1 by the lens 53 of the optical head 50. The fluorescent light beam K1 is reflected by the reflecting surface of the perforated mirror 52 and travels along the direction of arrow X. The fluorescent light beam K1 traveling in the direction of arrow X is incident on the PMT 90. The PMT 90 amplifies the fluorescent light beam K1 and photoelectrically detects it as the corresponding electric signal. The electric signal is amplified by the logarithmic amplifier 91 and is converted to a digital signal by the A/D converter 92.

If single horizontal scanning ends in this manner, the optical head 50 is returned to the original position thereof by the horizontal scanning means 60. While the optical head 50 is being returned to the original position, the vertical scanning means 70 moves the laser light source 21, the optical head 50, and the PMT 90 integrally in the direction of arrow Y. Next, by repeating the aforementioned horizontal scanning and vertical scanning, the entire surface of the array chip 1 is irradiated with the laser light L1, and the fluorescent light K1 corresponding to each position on the array chip 1 is converted to a digital signal and acquired as labeled data S1. The labeled data S1 is input to the analyzer 93.

If the horizontal scanning and vertical scanning end and the labeled data S1 is acquired from the array chip 1, the optical head 50 is returned to the initial position thereof. Next, the array chip 1' with known cDNAs hybridized with the labeled cDNAs of the subject B is placed on the sample tray 20 and reading is performed in the same way as for the array chip 1 in order to acquire labeled data S2. The labeled data S2 is input to the analyzer 93.

Figure 3:
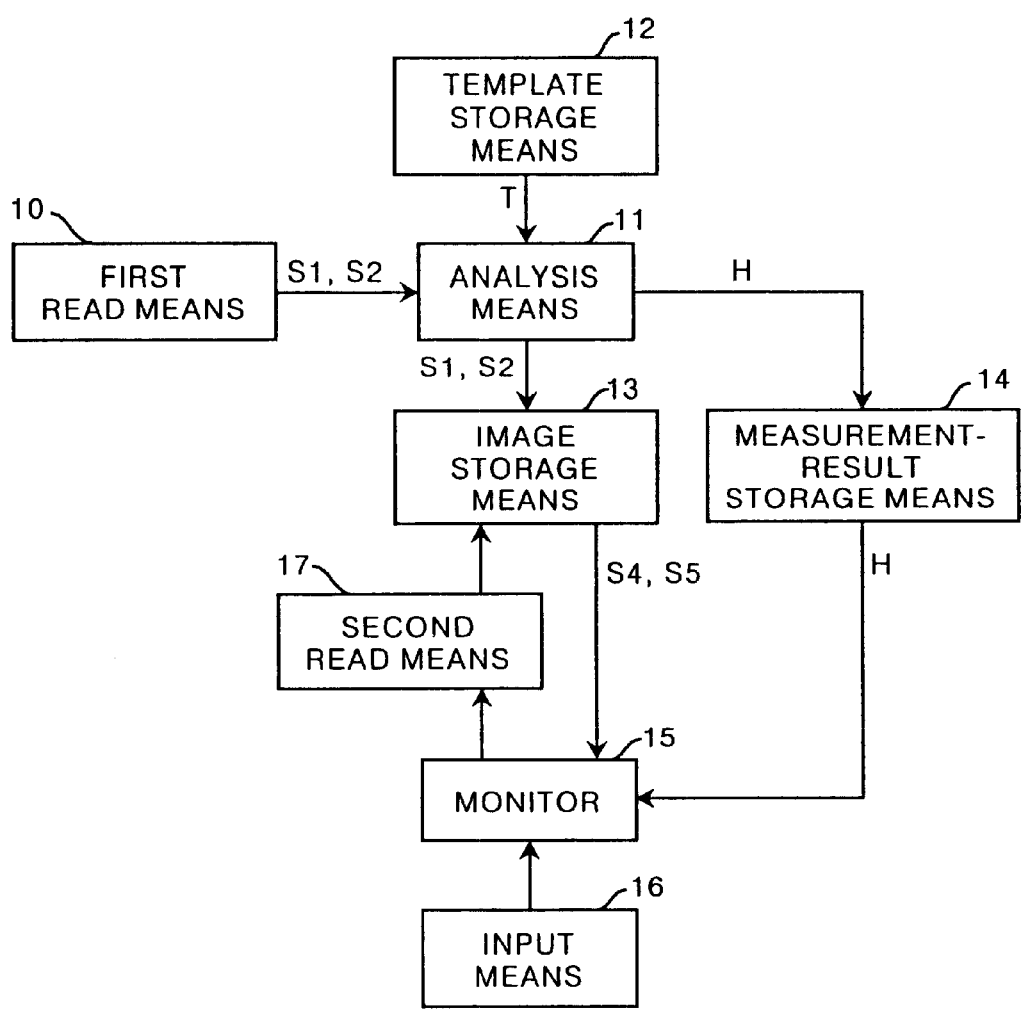
FIG. 3 is a block diagram showing the construction of the analyzer shown in FIG. 2.

FIG. 3 shows the construction of the analyzer 93. As shown in the figure, the analyzer 93 includes (1) first read means 10 for reading in the labeled data S1, S2; (2) analysis means 11 for analyzing the labeled data S1, S2 and outputting a measurement-result table H; (3) template storage means 12 for storing a plurality of templates T which become necessary in making an analysis in the analysis means 11, in accordance with the types of the array chips 1, 1' to be used; (4) image storage means 13 for storing the labeled data S1, S2 caused to correspond to addresses by the template T as described later; (5) measurement-result storage means 14 for storing the measurement-result table H; (6) a monitor 15 for displaying the measurement-result table H and images; (7) input means 16 consisting of a keyboard and a mouse which perform various inputs, and (8) second read means 17 for reading out images at spot positions, corresponding to a measurement result selected as described later, from the image storage means 13 as image data S4, S5.

Figure 4:
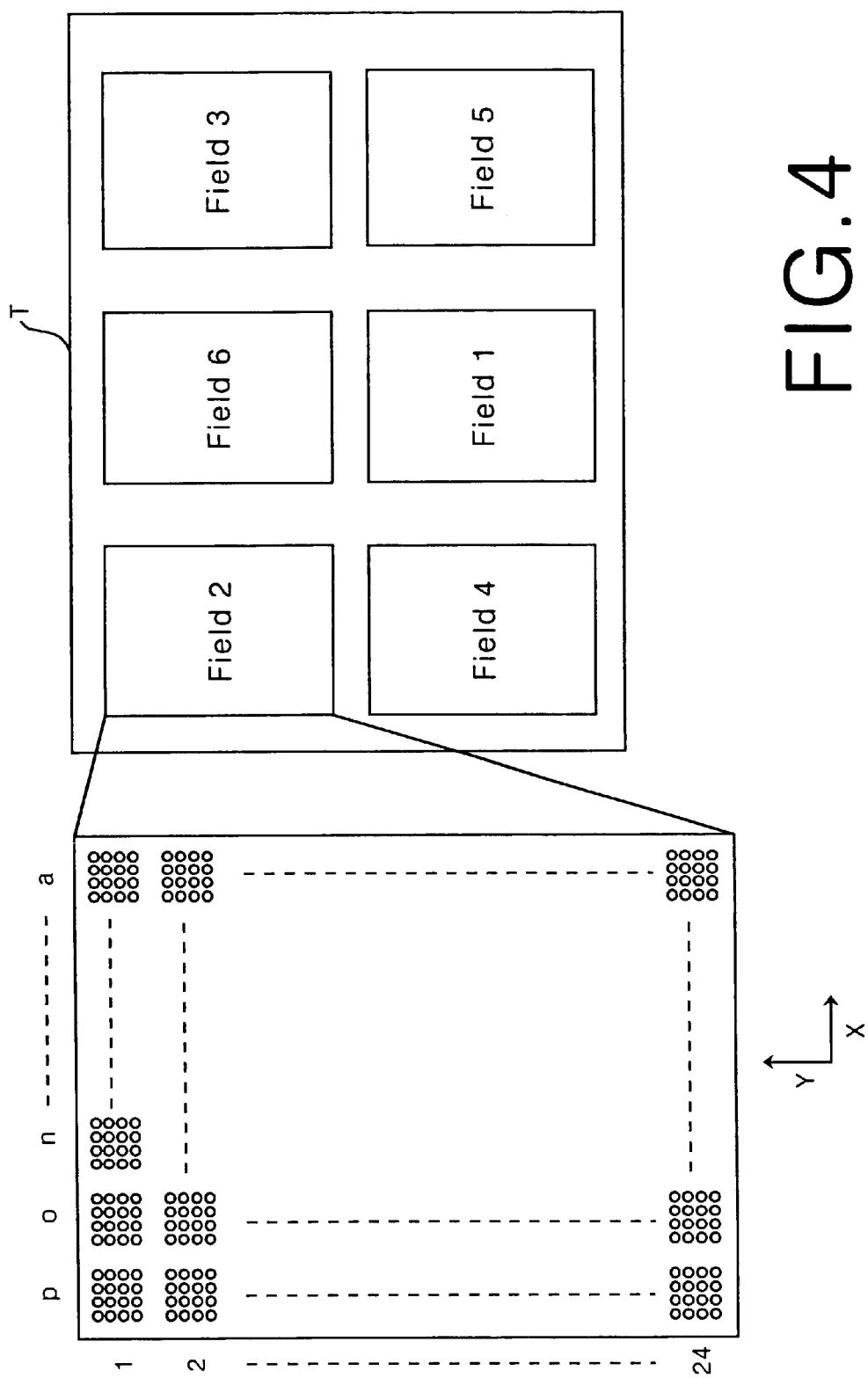
FIG. 4 is a schematic diagram showing a template employed in the preferred embodiment.
Figure 5:
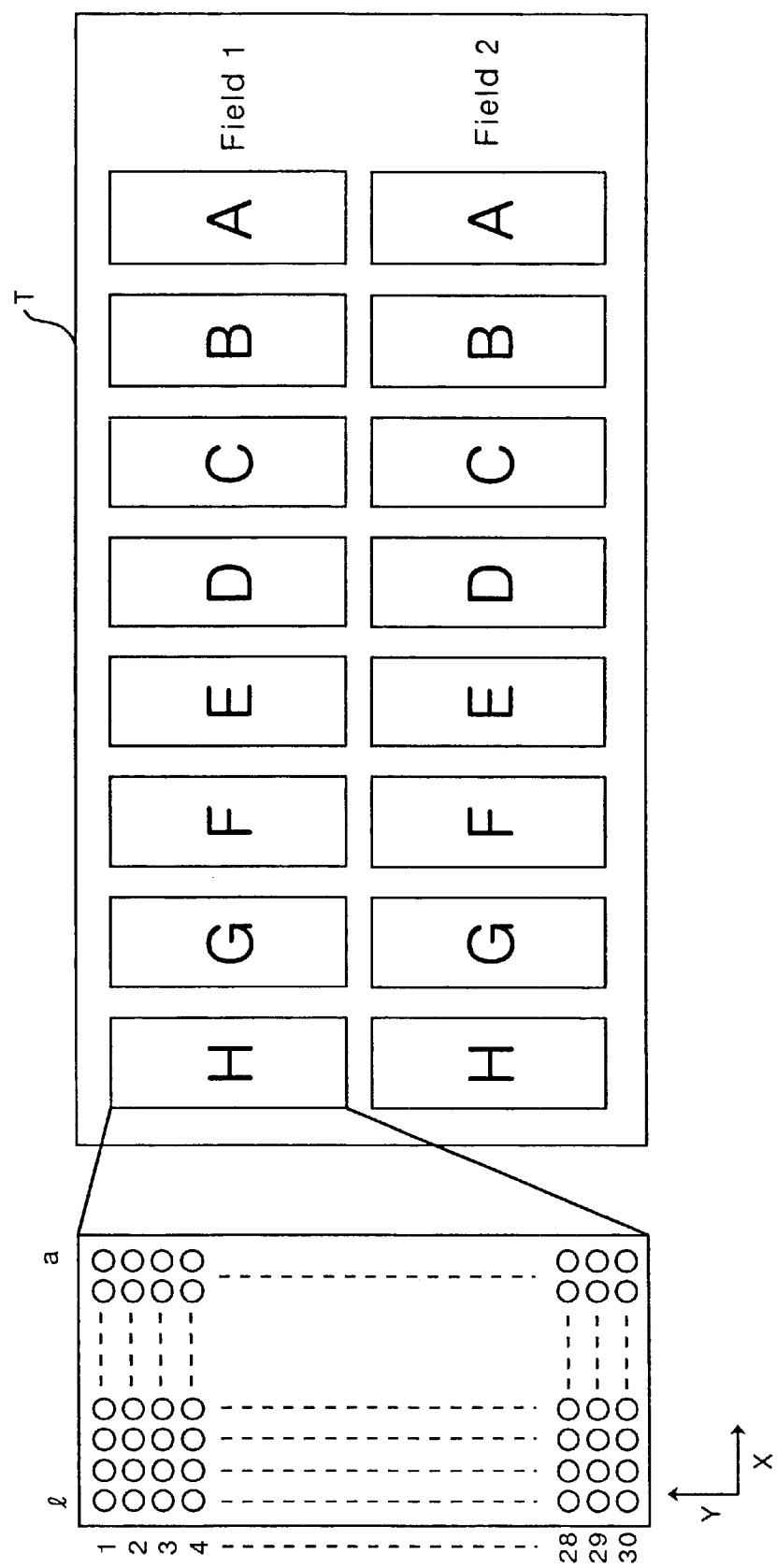
FIG. 5 is a schematic diagram showing another template.
Figure 6:
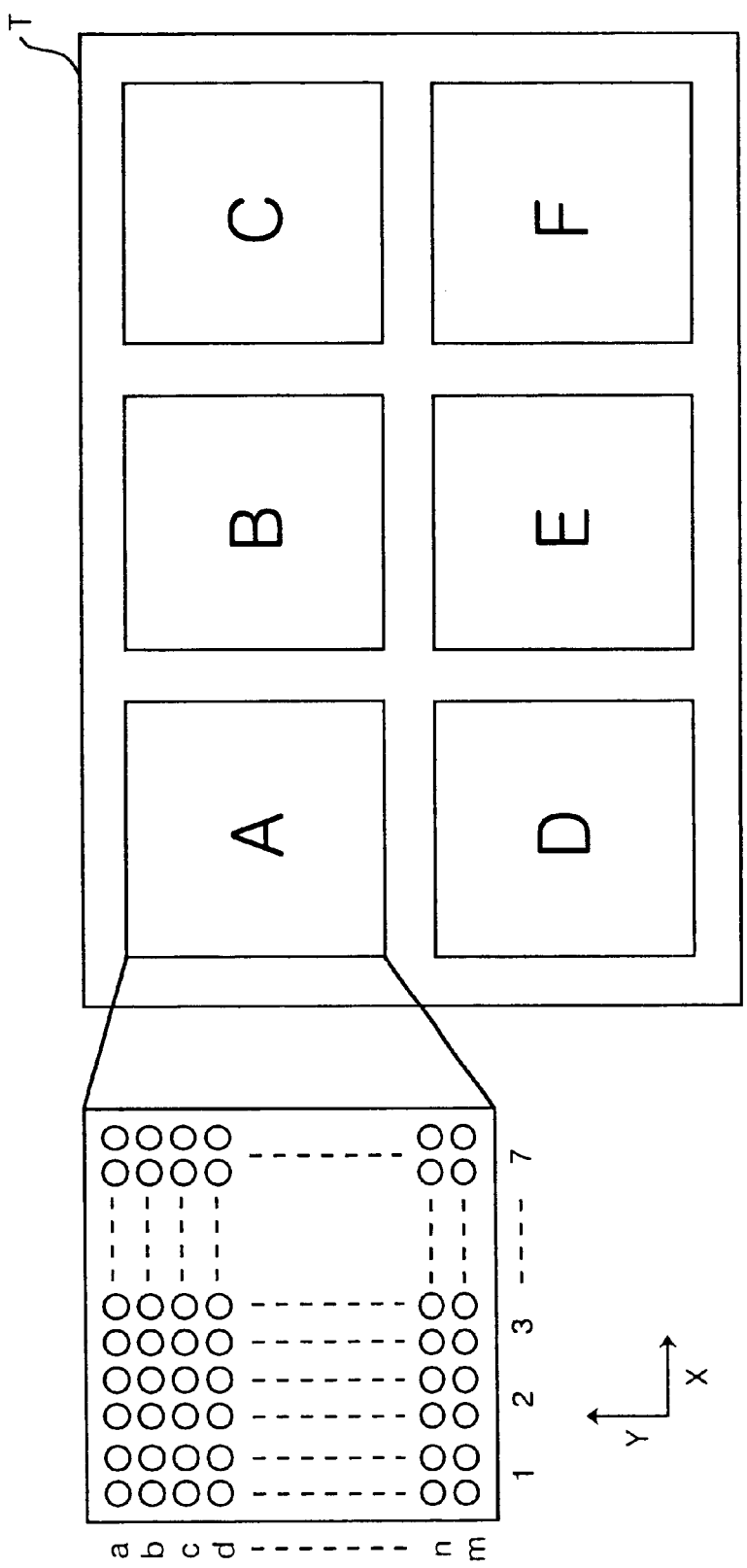
FIG. 6 is a schematic diagram showing still another template.

The template storage means 12 stores a plurality of templates T, in each of which a plurality of circular ROIs are disposed at positions corresponding to spot positions on the array chips 1, 1'. That is, the disposition of spot positions on the array chips 1, 1' varies depending upon manufacturers for array chips 1, 1' and test purposes, and in accordance with the types of the array chips 1, 1' to be used, a plurality of templates T are stored in the template storage means 12, for example, as shown in FIGS. 4 to 6. Note that circular portions on the templates T shown in FIGS. 4 to 6 represent ROIs corresponding to spot positions.

Also, each ROI on the template T is given an address number. For instance, the template T shown in FIG. 4 is divided into 6 fields, field 1 to field 6. Each field has 16×24 ROI blocks, each of which has 4×4 ROIs. The 16×24 ROI blocks are given address Nos. a to p in the X direction and address Nos. 1 to 24 in the Y direction. The position of the ROI block in each field can be represented, for example, as a-1. Furthermore, in each ROI block, 8 kinds of paired cDNAs are disposed and the same pattern number is given to the spot positions at which the same cDNA is disposed. Therefore, for example, in the case where the pattern number in the ROI block is 2, the position of the ROI on the template shown in FIG. 4 can be specified, for example, with "Field 1, a-2, 2" as an address number.

In addition, the template T shown in FIG. 5 is divided into 2 fields, field 1 and field 2. Each field is further divided into 8 regions A to H, each of which has 12×30 ROIs. The 12×30 ROIs are given address Nos. a to l in the X direction and address Nos. 1 to 30 in the Y direction. The position of the ROI on the template shown in FIG. 5 can be specified, for example, with "Field 1, B, a-1" as an address number.

Furthermore, the template T shown in FIG. 6 is divided into 6 regions A to F. Each region has 7 ROI blocks in the X direction, each of which has 2×14 ROIs. The ROI blocks are given address Nos. a to m in the Y direction and address Nos. 1 to 7 in the X direction. Note that in the template T shown in FIG. 6, the ROI block numbers have the same cDNA when they are the same. Therefore, the position of the ROI on the template shown in FIG. 6 can be specified, for example, with "A, 1-a" as an address number.

The operation of the analyzer 93 will hereinafter be described. The type of the array chips 1, 1' used is first supplied from the input means 16 to the analysis means 11. In the analysis means 11, the template T, on which ROIs are disposed at positions corresponding to the spot positions on the array chips 1, 1', is read out from the template storage means 12 and disposed on the images represented by the labeled data S1, S2. Note that in the preferred embodiment, the template T of FIG. 4 corresponding to the array chips 1, 1' is used. When employing an array chip that corresponds to the template T shown in FIG. 5 or 6, the template T corresponding to this array chip is read out from the template storage means 12. Next, the position of the template T is adjusted so that the circular ROIs on the template T fit the spot positions on the images. In the array chips 1, 1', spotting is performed on the spot positions, but there are cases where a slight positional mismatch occurs in each spot. Therefore, the operation of aligning the ROI with the spot position is performed to make an accurate measurement at each spot. More specifically, the position of the ROI is aligned with the spot position, by rotation, horizontal and vertical movements, and enlargement and reduction of the template T. This alignment may be performed automatically. Also, the alignment may manually be performed by displaying the labeled data S1, S2 and the template T on the monitor 15 and operating the mouse of the input means 16. Note that before this alignment, it is preferable to display the labeled data S1, S2 and remove abnormal portions that have an abnormal signal value at each spot position, because of spots that become obscure or spread when the DNAs of the subjects A, B are spotted on the array chips 1, 1', a large quantity of fluorescent light, unnecessary spots that remain after spots have been washed with a predetermined solution as described above, and the like. With this alignment, each spot position is given an address number corresponding to the address number of the template T. Also, in the images represented by the labeled data S1, S2, each pixel position can be represented as a coordinate value and is therefore caused to correspond to a coordinate value on the image representing a central position between address numbers. The correspondence information representing a result of this correspondence is given to the labeled data S1, S2.

If alignment is performed in this way, a measurement of density at each spot position is made in response to an instruction from the input means 16. More specifically, signal values at an area enclosed by a ROI are integrated and this integrated signal value is detected as a value of density for that spot position. At this time, it is preferable to remove a background density value, i.e., a density value for the carrier 2 of the array chips 1, 1' from the detected density value. If density values are detected for all the ROIs set to the labeled data S1, S2, a ratio of the density values obtained at spot positions corresponding to each other between the labeled data S1, S2 is calculated. Here, if a density value for the labeled data S1 obtained at a specific spot position is taken as N1 and a density value for the labeled data S2 obtained at a spot position corresponding to the specific spot position as N2, this ratio is calculated as N2/N1. In the order of a greater ratio, the address numbers for 50 spot positions, for example, are caused to correspond to the values of ratios and this relation of correspondence is generated as a measurement-result table H. The measurement-result table H is stored in the measurement-result storage means 14. Also, the labeled data S1, S2 are given the above-mentioned correspondence information and stored in the image storage means 13.

Figure 7:
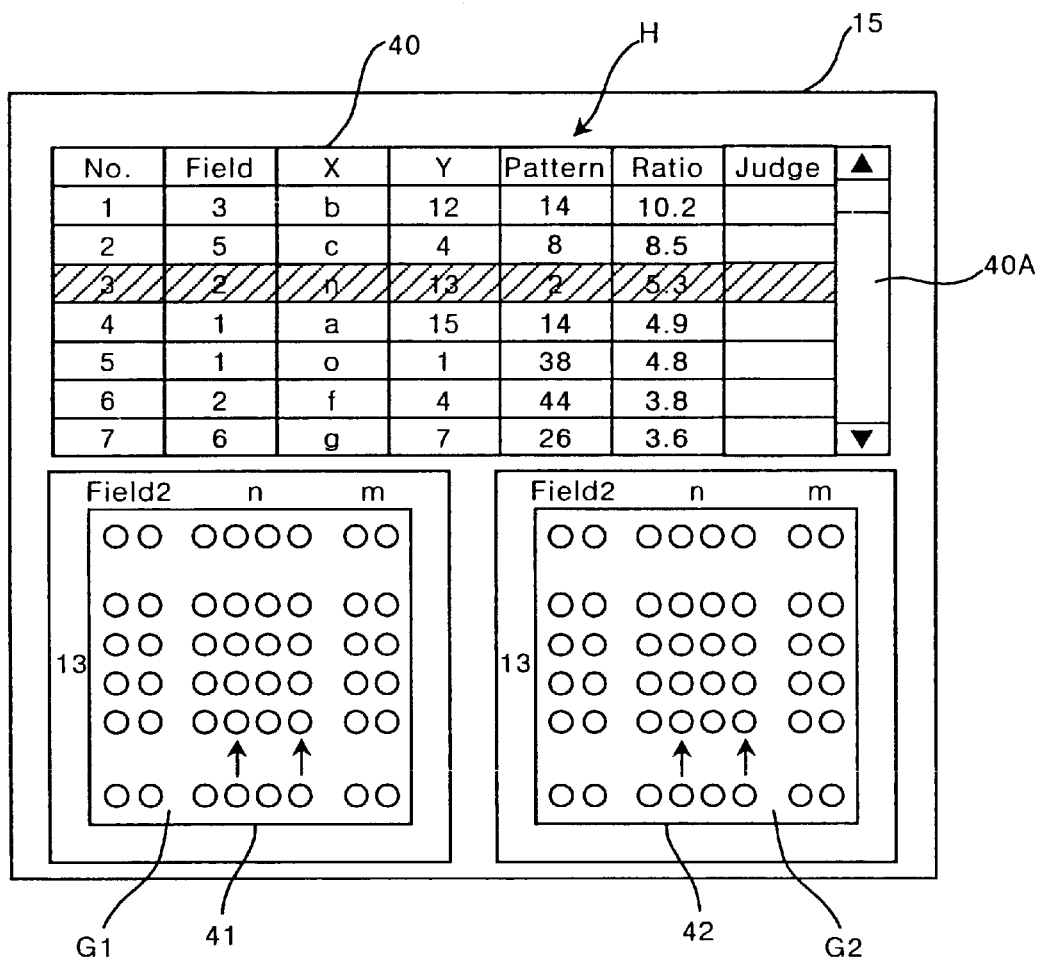
FIG. 7 is a diagram showing measurement results and images obtained according to the preferred embodiment.

If an instruction to display both the measurement-result table H and the labeled data S1, S2 is input from the input means 16, the measurement-result table H is read out from the measurement-result storage means 14 and the labeled data S1, S2 from the image storage means 13 and they are displayed on the monitor 15. FIG. 7 shows the displayed state of the measurement-result table H and the labeled data S1, S2. As shown in the figure, the 7 higher rows in the measurement-result table H are displayed on the window 40 of the monitor 15 and all the rows can be displayed by operating a scroll bar 40A. The measurement-result table H is provided with items of row number (No.), field number (Field), address number in X and Y directions (X, Y), pattern number (Pattern), ratio calculated (Ratio), and judgement (Judge). Note that the "Judge" item is a blank column for inputting operator's evaluation. Also, the images G1, G2 at a spot position corresponding to the row selected in the measurement-result table H are displayed on the windows 41, 42, respectively. Notice that in FIG. 7, row No.3 has been selected and the images G1, G2, for a spot block corresponding to the ROI block at the position of "Field 2, n−13" which is a spot position corresponding to the row No. 3, have been displayed on the windows 41, 42.

The operator observes the measurement-result table H and the images G1, G2 thus displayed, and inputs the evaluation of observation to the "Judge" column in the measurement-result table H. This evaluation may be performed by inputting "Good", which represents that the result of the measurement and the state of the image shows that the target gene is manifested, "NG", which represents non-manifestation, or "?", which represents that a judgement cannot be made, from the input means 16. Here, it is preferable that the input of the evaluation be performed so that "Good" is input when "G" is pressed on the keyboard and "NG"is input when "N" is pressed. By selecting the rows in sequence, evaluations are made, while reference is being made to the measurement-result table H and the images G1, G2.

According to the preferred embodiment, as described above, the template T, on which ROIs are disposed at positions corresponding to the spot positions on the array chips 1, 1' used, is read out from the template storage means 12 in which various types of templates are stored. Therefore, if various types of templates corresponding to array chips with a possibility of being used are stored in the template storage means 12, density values at spot positions can be detected from the labeled data S1, S2 without generating a new template, regardless of the array chip employed.

Note that in the above-mentioned embodiment, there are cases where a template, on which ROIs are disposed at positions corresponding to the spot positions on the array chips 1, 1' used, has not been stored in the template storage means 12. For this reason, the template storage means 12 may be provided with a template generation means for generating a new template on which ROIs are disposed at positions corresponding to spot positions on the array chips 1, 1'. In this case, there are various attributes of spot positions, such as the number of layers (e.g., one layer in which spots are disposed in matrix form, two layers in which a plurality of spot blocks consisting of 4×4 spots are disposed as shown in FIG. 4, etc.), the number of spots, the number of spot blocks, a method of expressing addresses, the number of fields, the number of spots within a field, paired spots shown in FIG. 6, the number of paired spots, whether or not spots are for signal detection, whether or not spots are for positioning, an attribute of measurement for each spot as to whether or not spotting is performed, and the like. These attributes vary between manufactures for array chips. Therefore, it is desirable that the template generation means be capable of generating a template in view of these attributes.

While, in the above-mentioned embodiment, cDNA has been employed as a specific binding substance and cDNA originated from a cell has been employed as an organism-originated substance, the present invention is not limited to this example.

Also, in the above-mentioned embodiment, while the analyzer 93 calculates the ratio of the labeled data S1, S2, the analyzer 93 may calculate the differences between the labeled data S1, S2 and generate a table in which 50 spot positions are caused to correspond to the values of the differences in the order of a greater difference.

In addition, in the above-mentioned embodiment, although analyses have been made by employing two array chips 1, 1', analyses may be made with respect to two kinds of subjects A, B by employing a single array chip in which two sets of pluralities of known cDNAs differing from one another are disposed.

Furthermore, in the above-mentioned embodiment, analyses have been made with respect to two kinds of subjects A, B. However, with respect to three or more kinds of subjects, it is possible to read the array chips, make analyses, and display the measurement-result table H and images in the same way as the aforementioned.

Finally, in the above-mentioned embodiment, the fluorescent dye has been employed as a labeling substance, but it is also possible to employ a radioactive isotope.

What is claimed is:

1. A method for detecting an organism-originated substance comprising the steps of:

respectively binding organism-originated substances of a subject labeled with a labeling substance to a plurality of known specific binding substances differing from one another, the specific binding substances being disposed at a plurality of predetermined positions on a carrier on an array chip;

obtaining an image represented by labeling signals emitted from the labeling substances of said organism-originated substances bound to said specific binding substances;

setting a template of a type corresponding to said array chip onto said image, the template having regions of interest disposed at positions corresponding to said plurality of predetermined positions on said array chip where the specific binding substances are disposed; and detecting values of said labeling signals at positions on said image which correspond to said regions of interest;

wherein said step of setting the template comprises reading out one template from a plurality of templates stored in a template storage means, and based on said template read out, said labeling values are detected.

2. The method as set forth in claim 1, further comprising the step of generating a new template and storing said new template in said template storage means.

3. The method according to claim 1, further comprising a step of adjusting at least one of a template orientation and a template size such that the regions of interest of said template overlap with labeling signals emitted from the labeling substances of said organism-originated substances bound to said specific binding substances.

4. The method according to claim 1, further comprising steps of:

assigning an identifier to each region of interest; and selectively displaying, for one or more regions of interest, the identifier, the labeling signal information and binding substance characteristic information corresponding to the region of interest.

* * * * *